(12) United States Patent
Nakano et al.

(10) Patent No.: US 8,689,608 B2
(45) Date of Patent: Apr. 8, 2014

(54) THERMAL GAS SENSOR

(75) Inventors: Hiroshi Nakano, Tokai (JP); Masamichi Yamada, Hitachinaka (JP); Masahiro Matsumoto, Hitachi (JP); Keiji Hanzawa, Mito (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 492 days.

(21) Appl. No.: 12/973,376

(22) Filed: Dec. 20, 2010

(65) Prior Publication Data
US 2011/0154885 A1  Jun. 30, 2011

(30) Foreign Application Priority Data
Dec. 28, 2009 (JP) ................... 2009-296665

(51) Int. Cl.
*G01N 25/18* (2006.01)
(52) U.S. Cl.
USPC .......................... 73/25.03; 73/25.05
(58) Field of Classification Search
USPC .......... 73/25.03, 25.05, 31.01, 31.06
See application file for complete search history.

(56) References Cited

U.S. PATENT DOCUMENTS

| | | | | | |
|---|---|---|---|---|---|
| 4,717,811 | A | * | 1/1988 | Fujii | 219/497 |
| 4,902,138 | A | * | 2/1990 | Goeldner et al. | 374/44 |
| 5,551,283 | A | | 9/1996 | Manaka et al. | |
| 5,772,321 | A | * | 6/1998 | Rhodes | 374/44 |
| 5,837,884 | A | | 11/1998 | Kimura et al. | |
| 7,165,441 | B2 | * | 1/2007 | Bauer et al. | 73/25.03 |
| 7,452,126 | B2 | * | 11/2008 | Arndt et al. | 374/44 |
| 7,780,343 | B2 | * | 8/2010 | Chen et al. | 374/45 |
| 7,963,147 | B2 | * | 6/2011 | Jun et al. | 73/31.06 |
| 8,359,919 | B2 | * | 1/2013 | Matsumoto et al. | 73/335.05 |
| 2005/0199041 | A1 | * | 9/2005 | Weber et al. | 73/31.06 |
| 2009/0016403 | A1 | * | 1/2009 | Chen et al. | 374/45 |

FOREIGN PATENT DOCUMENTS

| | | |
|---|---|---|
| JP | 2889909 B2 | 2/1999 |
| JP | 3343801 B2 | 8/2002 |
| JP | 2007-248356 A | 9/2007 |
| JP | 2008-20193 A | 1/2008 |
| JP | 2009-168649 A | 7/2009 |
| WO | WO 2006/063427 A1 | 6/2006 |

OTHER PUBLICATIONS

English Language Machine Translation of the Detailed Description of JP 2009-168649. Translated on Jul. 10, 2013 at <http://www.jpo.go.jp/index.htm>.*
R. Jachowicz and J. Weremczuk, "Sub-cooled water detection in silicon dew point hygrometer," Sensors and Actuators 85 (2000) 75-83.*
European Search Report dated Feb. 22, 2013 (Three (3) pages).

* cited by examiner

*Primary Examiner* — Lisa Caputo
*Assistant Examiner* — Punam Roy
(74) *Attorney, Agent, or Firm* — Crowell & Moring LLP

(57) ABSTRACT

The present invention provides a high-responsiveness and high-accuracy thermal gas sensor configured to enable gas to be analyzed based on a variation in heat conductivity. The thermal gas sensor includes a substrate 2 with a cavity portion 5, a thin-film support 6 stacked in the cavity portion and comprising a plurality of insulating layers 8a and 8b, and a first heating member 3 and a second heating member 4 both sandwiched between the insulating layers in the thin-film support. The second heating member is located around a periphery of the first heating member. The first heating member is controlled to a temperature higher than a temperature to which the second heating member is controlled. The concentration of ambient gas is measured based on power applied to the first heating member.

13 Claims, 15 Drawing Sheets

THERMAL GAS SENSOR

BACKGROUND OF THE INVENTION

1. Field of the Invention

The present invention relates to a thermal gas sensor configured to measure components of a gas to be measured, based on a variation in heat conduction in the gas.

2. Background Art

A thermal gas sensor is used to analyze a gas using a variation in heat conduction in the gas. The variation in the heat conduction in the gas is measured based on the amount of heat radiated by a heating member exposed to the gas.

Thermal gas sensors are used in various technical fields. For internal combustion engines for automobiles and the like, there has been a demand to accurately measure the flow rate, temperature, and pressure of intake air as well as an environmental condition such as humidity in order to reduce fuel consumption. Thermal gas sensors are also used to detect the concentration of hydrogen in internal combustion engines for automobiles that use hydrogen as fuel in order to allow the internal combustion engine to be optimally driven.

Thermal gas sensors serving as gas sensors that measure the humidity or the concentration of gas as described above avoid absorbing moisture and are excellent in environment resistance such as contamination resistance and prolonged stability. JP Patent No. 2889909 as a prior art document for such a thermal gas sensor discloses a humidity sensor based on a variation in the resistance value of a resistor heated in an atmosphere and configured to compare a voltage generated across the resistor at a high temperature with a voltage generated across the resistor at a low temperature to sense the humidity, wherein at the low temperature, the variation in resistance is affected only by the atmosphere temperature, and at the high temperature, the variation in resistance is sensitive to the temperature and humidity of the atmosphere.

Furthermore, JP Patent No. 3343801 discloses a humidity sensor including heating means for heating a temperature-sensitive resistor using a heating member. The heating means applies two pulse voltages to the heating member in order within a given time to switch the temperature of the temperature-sensitive resistor between a first value of at least 300° C. and a second value of 100° C. to 150° C. The humidity sensor detects the humidity based on an output voltage associated with a drop in the voltage of the temperature-sensitive resistor at each of the temperatures.

The humidity sensors disclosed in JP Patent Nos. 2889909 and 3343801 are configured to heat the same heating member or temperature-sensitive resistor to the low temperature (second temperature) and to the high temperature (first temperature) in a time division manner.

The configuration that heats the same heating member or temperature-sensitive resistor in a time division manner as described above has the advantage of saving power. However, this configuration is disadvantageous in that an amount of time is required to heat and naturally cool the heating member or temperature-sensitive resistor to the different temperatures, thus reducing response speed.

In particular, the measurement of humidity of intake air for an internal combustion engine requires instantaneousness because the humidity is important data used for the instantaneous calculations of fuel injection time and the like. In connection with such an application, the response speed is a challenge for the conventional humidity sensors disclosed in JP Patent Nos. 2889909 and 3343801.

Furthermore, a signal corresponding to the humidity is conventionally obtained by calculations that use various parameters such as the output voltages associated with drops in the voltage of the temperature-sensitive resistor at the first and second temperatures and the premeasured resistance value of the temperature-sensitive resistor. This is to eliminate the adverse effect of a variation in gas temperature. Thus, when prolonged use deteriorates the resistance value of the temperature-sensitive resistor, errors disadvantageously occur in the parameters to increase the errors in calculations.

Thus, an object of the present invention is to solve the problems with the above-described conventional examples and provide a high-responsiveness and high-accuracy thermal gas sensor that can be used in various environmental conditions.

SUMMARY OF THE INVENTION

To accomplish this object, a thermal gas sensor according to the present invention is configured as follows. A thin-film support is formed in a cavity portion of a substrate. A first heating member and a second heating member are formed on the thin-film support. The second heating member is located around the periphery of the first heating member. The first heating member is controlled to a temperature higher than a temperature to which the second temperature is controlled. The condition of ambient gas is measured based on heating power for the first heating member. Thus, the peripheral temperature of the first heating member detecting a variation in heat conduction in gas can be maintained at a predetermined temperature by the second heating member. This enables a reduction in the adverse effect of a variation in gas temperature and eliminates the need to heat the heating member to the different temperatures in a time division manner. Furthermore, response speed can be increased.

Moreover, the second heating member is formed to surround the first heating member on all sides thereof, and an area in which the second heating member is laid is formed to be larger than an area in which the first heating member is laid. Thus, the temperature of the gas near the first heating member can be more stably maintained at a predetermined temperature. This enables the accuracy of the gas sensor to be improved.

Moreover, heating is controlled so as to make the difference in temperature between the first heating member and the second heating member constant. This allows accurate detection of a variation in the amount of heat radiated by the first heating member which variation results from a variation in the heat conductivity of the gas.

The present invention serves to reduce the adverse effect of the variation in gas temperature and provides a high-responsiveness and high-accuracy thermal gas sensor. The present invention can also simplify a driving circuit, allowing reliability to be improved.

Figure 1:
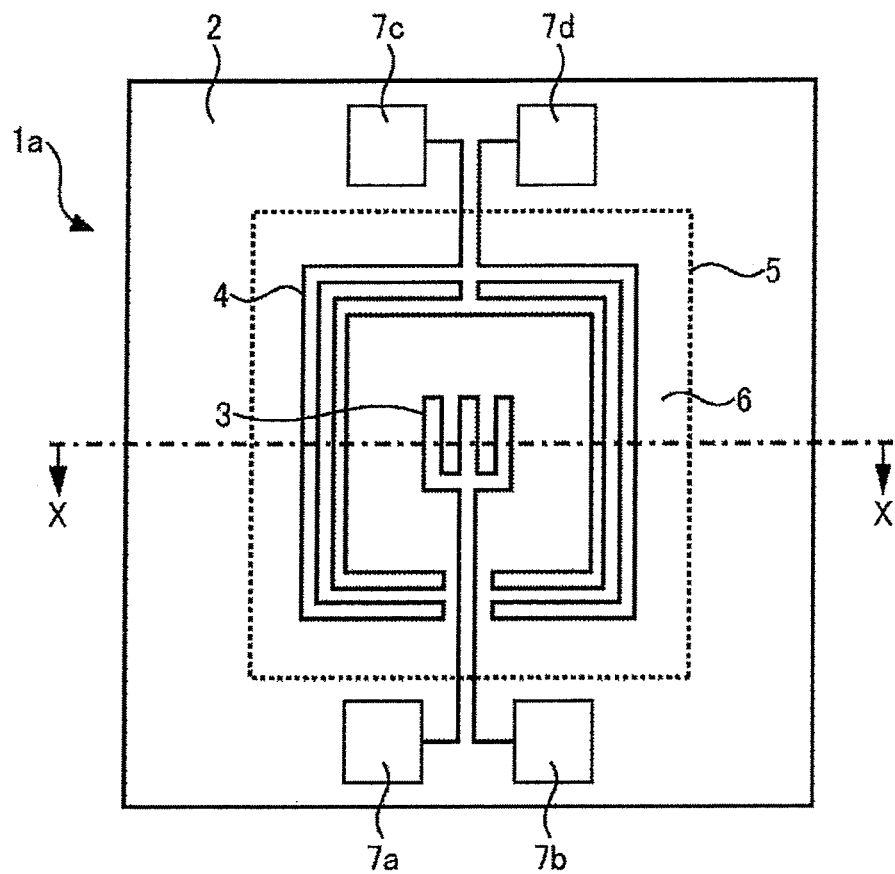
FIG. 1 is a plan view of a sensor of a thermal gas sensor showing a first embodiment.

DESCRIPTION OF SYMBOLS 1a, 1b, 1c Thermal gas sensors
2 Substrate
3, 4 Heating members
5, 47, 48 Cavity portions
6 Thin-film support
7a to 7j Electrodes
8a, 8b Insulating layers
9a to 9f Fixed-value resistors
10a, 10b Differential amplifiers
11a, 11b Transistors
12, 15 Power sources
14a to 14e Bridge circuits
23, 24, 34, 35, 36 Temperature sensors
37 Thermal airflow rate sensor
38 Driving LSI
39 Base member
40 Housing member
41 Bonding wire
42 Terminal section
43 Airflow
44 Inner layer conductor
45 Sub-passage
46 Thermal flowmeter
49 Composite sensor
51 Intake pipe

DETAILED DESCRIPTION OF THE PREFERRED EMBODIMENTS

Embodiments of the present invention will be described below based on the drawings. In the embodiments, an example of an intake system for an internal combustion engine for an automobile will be described which is applied to a thermal gas sensor configured to measure the humidity of intake air.

First Embodiment

Figure 2:
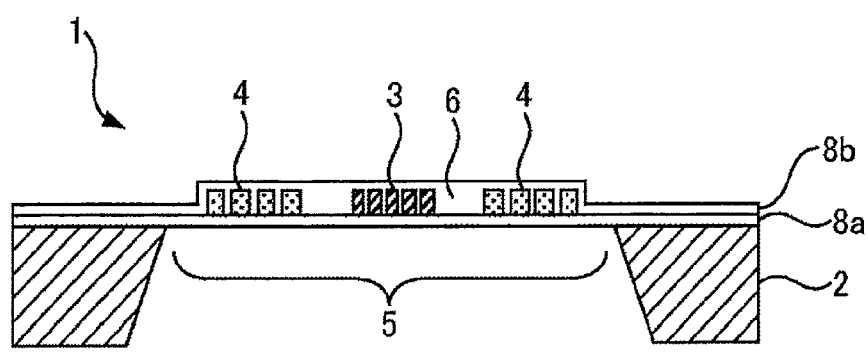
FIG. 2 is a sectional view taken along line X-X in FIG. 1.

FIG. 1 is a plan view of sensor elements of a thermal gas sensor showing a first embodiment. FIG. 2 is a sectional view taken along line X-X in FIG. 1.

A thermal gas sensor 1a includes a substrate 2 which is formed of a single-crystal silicon. As shown in FIG. 1, a cavity portion 5 is formed in the substrate 2. A first heating member 3 and a second heating member 4 are laid in the cavity portion 5. Furthermore, a thin-film support 6 configured to support the heating members is formed to lie over the cavity portion in the substrate 2.

Here, the thin-film support 6 is formed of insulating layers 8a and 8b stacked on the top surface of the substrate 2 as shown in FIG. 2. The heating members 3 and 4 are interposed between the insulating layers 8a and 8b. The heating member 4 is located so as to surround the periphery of the heating member 3.

When the heating member 4 is thus located so as to surround the periphery of the heating member 3, the ambient temperature of the heating member 3 is kept equal to the temperature (T2) of the heating member 4. This enables a further reduction in the dependence of the ambient temperature T3. Preferably, the heating member 4 is located so as to surround the heating member 3 on all sides thereof.

Furthermore, each of the heating members 3 and 4 comprises a resistor having a very small width, extending along the plane of the thin-film support 6, and including a plurality of turnup portions. The heating members 3 and 4 are electrically connected to electrodes 7a, 7b, 7c, and 7d formed on the substrate 2 for connection to an external circuit.

A material for the heating members 3 and 4 is selected from, for example, platinum (Pt), tantalum (Ta), molybdenum (Mo), and silicon (Si), which are stable at high temperatures (which have high melting points). A material for the insulating layers 8a and 8b is selected from silicon oxide ($SiO_2$) and silicon nitride ($Si_3N_4$) and formed into a single layer or a laminate structure. Alternatively, the material for the insulating layers 8a and 8b may be selected from a resin material such as polyimide, ceramic, and glass and formed into a single layer or a laminate structure. Furthermore, a material for the electrodes 7a, 7b, 7c, and 7d is selected from aluminum (Al), gold (Au), and the like.

The heating members 3 and 4, the insulating layers 8a and 8b, and the electrodes 7a, 7b, 7c, and 7d are formed using a semiconductor micromachining technique that utilizes photolithography and an anisotropic etching technique. In particular, the cavity portion 5 is formed by anisotropically etching the single-crystal silicon substrate 2. Thus, metal that is tolerant to an alkali etching solution used for anisotropic etching may be used as the electrodes 7a to 7d.

Furthermore, when metal such as aluminum which offers no tolerance is used, preferably the electrodes 7a to 7d are formed of an alloy of aluminum and silicon so as to be tolerant to an alkali etching solution or a protect film may be formed on the electrodes 7a to 7d. Anisotropic etching may be performed after forming the protect film.

Figure 3:
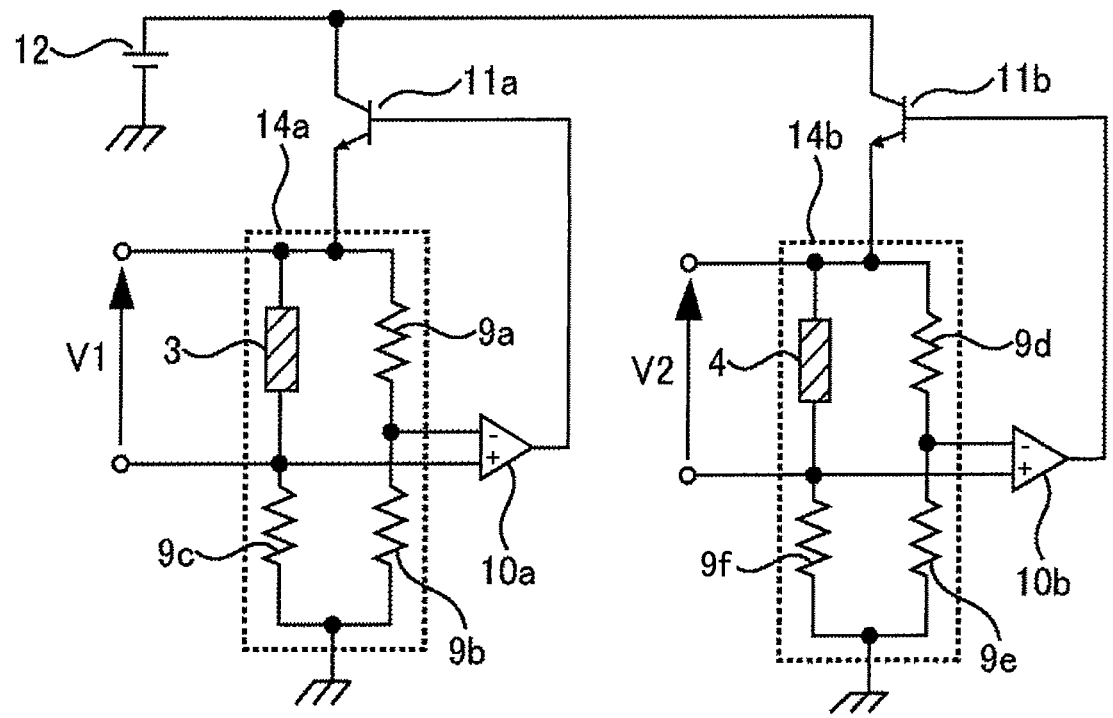
FIG. 3 is a diagram of a driving circuit for the thermal gas sensor showing the first embodiment.

FIG. 3 is a diagram of a driving circuit for the thermal gas sensor 1a. The operation of the thermal gas sensor according to the first embodiment will be described with reference to FIG. 3.

The driving circuit for the thermal gas sensor 1a is configured to supply heating current to the first heating member 3 and second heating member 4 so as to control the first heating member 3 to a first temperature T1, while controlling the second heating member 4 to a second temperature T2 lower than the first temperature.

The driving circuit for the thermal gas sensor 1a includes a first bridge circuit 14a and a second bridge circuit 14b, differential amplifiers 10a and 10b, and transistors 11a and 11b configured to allow heating current to flow through the heating members 3 and 4. In FIG. 3, reference numeral 12 denotes a power source.

The first bridge circuit 14a includes the heating member 3 and fixed-value resistors 9a, 9b, and 9c. More specifically, the first bridge circuit 14a includes a series circuit with the heating member 3 and the fixed-value resistor 9c connected together in series and a series circuit with the fixed-value resistors 9a and 9b connected together in series; the series circuits are connected together in parallel. Similarly, the second bridge circuit 14b includes the heating member 4 and fixed-value resistors 9d, 9e, and 9f. More specifically, the second bridge circuit 14b includes a series circuit with the heating member 4 and the fixed-value resistor 9f connected together in series and a series circuit with the fixed-value resistors 9d and 9e connected together in series; the series circuits are connected together in parallel.

In this case, in the first bridge circuit 14a, the potential of the connection end between the heating member 3 and the fixed-value resistor 9c and the potential of the connection end between the fixed-value resistors 9a and 9b are input to the differential amplifier 10a. The differential amplifier 10a outputs a voltage corresponding to the difference between the input voltages to a base electrode of the transistor 11a. The transistor 11a controls a current flowing between a collector and an emitter in accordance with the potential of the base electrode. The emitter electrode of the transistor 11a is connected between the heating member 3 and fixed-value resistor 9a in the first bridge circuit 14a to allow the collector-emitter current to flow through the first bridge circuit 14a. The resistance value of the fixed-value resistor 9a is set to be at least 10 times as large as that of the heating member 3. Thus, almost all of the current from the transistor 11a flows to the heating member 3, which is thus heated. This configuration feedback-controls the temperature of the heating member 3 to the first temperature T1, which is a constant temperature of about 300° C.

The temperature of the heating member 3 is set such that, based on the known temperature coefficient of resistance of the heating member 3, the ratio of the resistance value of the heating member 3 at the first temperature T1 to the resistance value of the fixed-value resistor 9c is equal to the ratio of the resistance value of the fixed-value resistor 9a to the resistance value of the fixed-value resistor 9b. When the temperature of the heating member 3 is lower than the first temperature T1, the transistor 11a is turned on to allow heating current to flow from the power source 12 to the heating member 3 via the transistor 11a.

Similarly, in the second bridge circuit 14b, the potential of the connection end between the heating member 4 and the fixed-value resistor 9f and the potential of the connection end between the fixed-value resistors 9d and 9e are input to the differential amplifier 10b. The differential amplifier 10b outputs a voltage corresponding to the difference between the input voltages to a base electrode of the transistor 11b. The transistor 11b controls a current flowing between a collector and an emitter in accordance with the potential of the base electrode. The emitter electrode of the transistor 11b is connected between the heating member 4 and fixed-value resistor 9d in the second bridge circuit 14b to allow the collector-emitter current to flow through the second bridge circuit 14b from the power source 12. The resistance value of the fixed-value resistor 9d is set to be at least 10 times as large as that of the heating member 4. Thus, almost all of the current from the transistor 11b flows to the heating member 4, which is thus heated. This configuration feedback-controls the temperature of the heating member 4 to the second temperature T2, which is a constant temperature of at least 100° C.

The temperature of the heating member 4 is set such that, based on the known temperature coefficient of resistance of the heating member 4, the ratio of the resistance value of the heating member 4 at the second temperature T2 to the resistance value of the fixed-value resistor 9f is equal to the ratio of the resistance value of the fixed-value resistor 9d to the resistance value of the fixed-value resistor 9e. When the temperature of the heating member 4 is lower than the second temperature T2, the transistor 11b is turned on to allow heating current to flow from the power source 12 to the heating member 4 via the transistor 11b.

Figure 4:
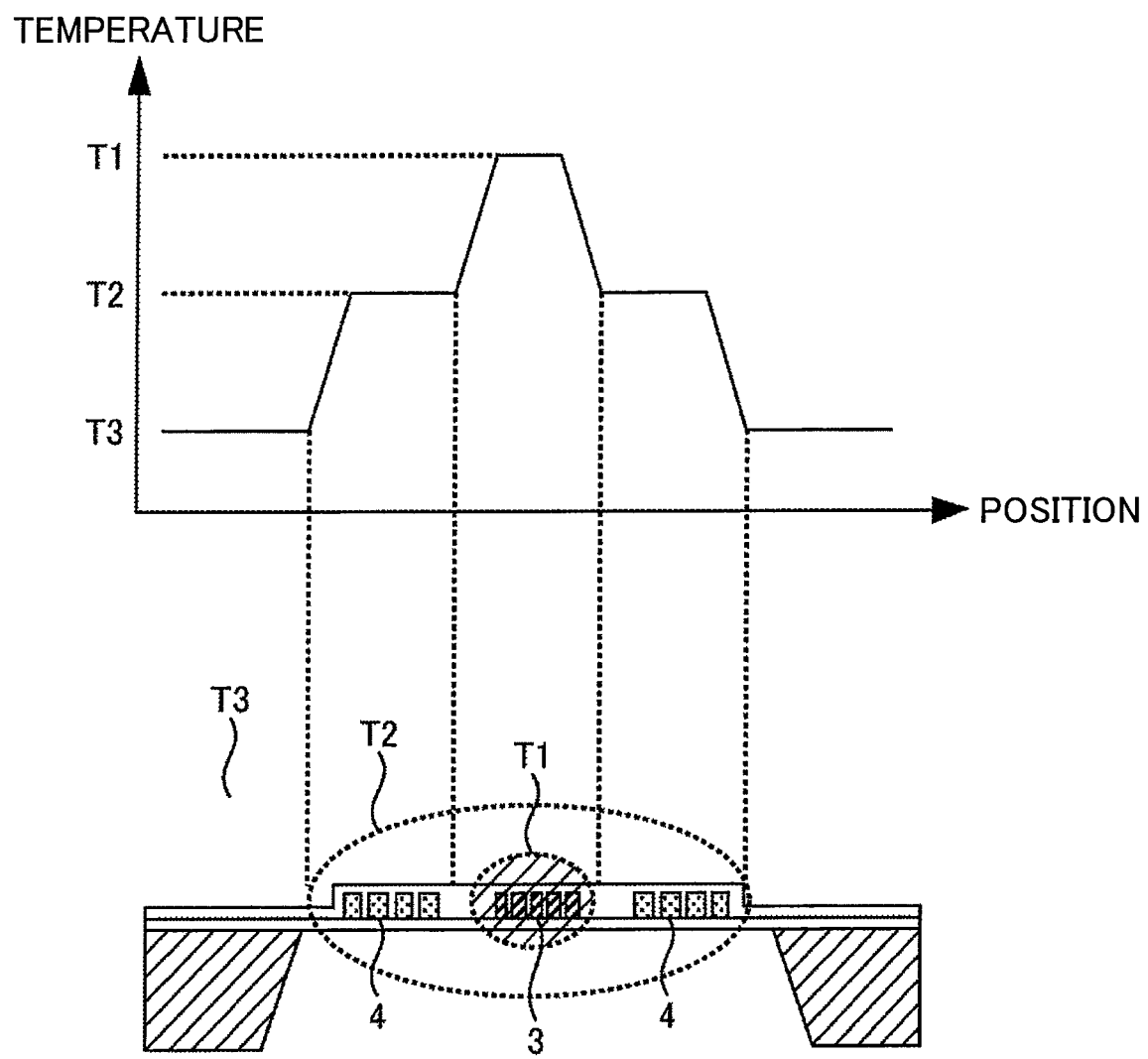
FIG. 4 is a diagram of the temperature distribution of the thermal gas sensor showing the first embodiment.

FIG. 4 shows a temperature condition near the heating members 3 and 4 controlled to the first temperature T1 and the second temperature T2, respectively. An ambient temperature T3 is the temperature of gas which is present around the thermal gas sensor 1a and which is to be measured. The ambient temperature T3 varies depending on environmental conditions such as the season. For intake air in an internal combustion engine for an automobile, the ambient temperature T3 varies between −40° C. and +125° C. The heating member 4 is heated to the temperature T2 by the driving circuit. Even with a variation in ambient temperature T3, the heating temperature of the heating member 4 is maintained at the value T2. The heating member 3 is heated by the driving circuit to the temperature T1, which is higher than T2.

Here, the amount Q1 of heat radiated to the gas by the heating member 3 and the amount Q2 of heat radiated to the gas by the heating member 4 are approximately expressed by:

$$Q1 = \lambda(T1-T2) \tag{1}$$

$$Q2 = \lambda(T2-T3) \tag{2}$$

Here, λ is a parameter indicating the heat conductivity of air and varying with the humidity. The expressions indicate that a variation in ambient temperature T3 significantly varies the radiation amount Q2 of the heating member 4, whereas the radiation amount Q1 of the heating member 3 is not affected by the ambient temperature T3. This is equivalent to the heating member 3 exposed to the air maintained at the constant temperature T2. Thus, since T1 and T2 are constant, the radiation amount Q1 of the heating member 3 depends only on λ. Since λ varies with the humidity, Q1 serves as a signal that depends on the humidity without being affected by a variation in ambient temperature T3.

Electric power P1 and electric power P2 provided to the heating members 3 and 4, respectively, are expressed by:

$$P1 = Q1 + QB1 + QG1 \tag{3}$$

$$P2 = Q2 + QB1 + QG2 \tag{4}$$

In Expressions (3) and (4), Q1 and Q2 denote the amounts of heat radiated to the ambient environment by heat conduction depending on the humidity. QB1 denotes the amount of heat transferred through the thin-film support 6 by heat conduction. QG1 and QG2 denote the amounts of heat transferred by natural convection and radiation.

Here, it is assumed that the thin-film support 6 has a small film thickness to provide ideally sufficient heat insulation, making the natural convection and radiation negligible. Then, the power P1 and power P2 provided to the heating members 3 and 4, respectively, are expressed by:

$$P1 = Q1 = V1^2/R1 \tag{5}$$

$$P2 = Q2 = V2^2/R1 \tag{6}$$

Here, V1 and V2 denote voltages applied to the heating members 3 and 4, respectively. R1 and R2 denote the resistance values of the heating members 3 and 4, respectively.

Moreover, based on Expressions (1), (2), (5), and (6), the following hold true.

$$V1^2 = \lambda(T1-T2) \cdot R1 \tag{7}$$

$$V2^2 = \lambda(T2-T3) \cdot R2 \tag{8}$$

In Expression (7), T1 and T2 are constant, and R1 is also constant. Thus, the voltage V1 applied to the heating member 3 serves as a signal that depends on λ that varies with the humidity, without being affected by the ambient temperature T3.

Figure 5:
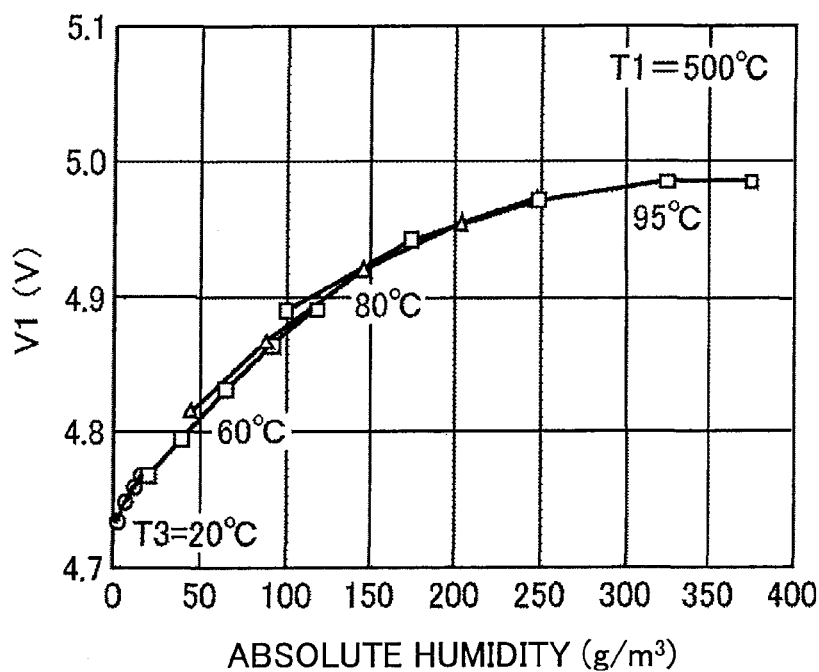
FIG. 5 is a diagram showing the results of experiments for the thermal gas sensor showing the first embodiment.
Figure 6:
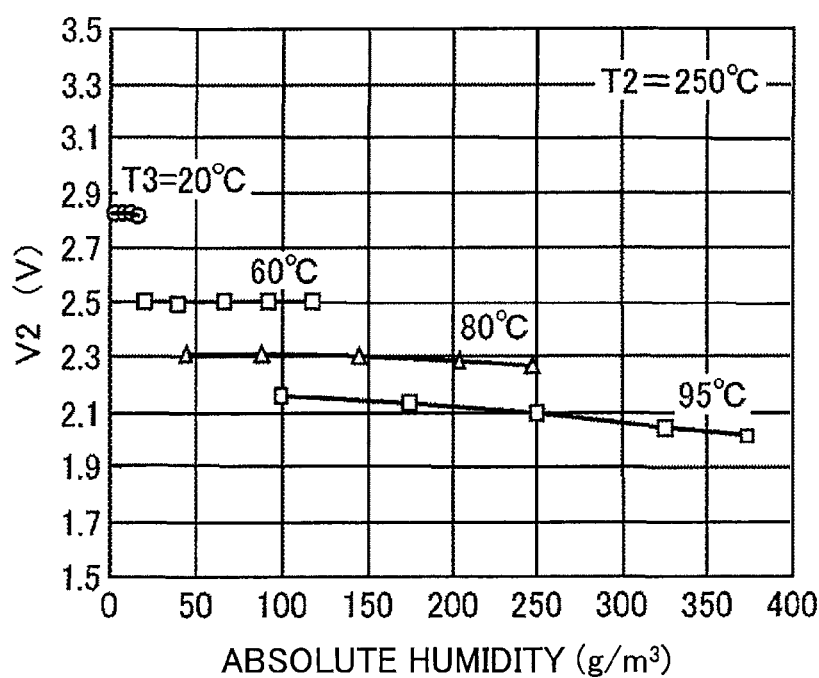
FIG. 6 is a diagram showing the results of experiments for the thermal gas sensor showing the first embodiment.

FIGS. 5 and 6 show the results of experiments according to the present embodiment. FIG. 5 shows the results of measurement of the voltage V1 applied to the heating member 3 when the thermal gas sensor according to the present embodiment is installed in the air and when the heating members 3 and 4 are heated so that T1=500° C. and T2=250° C., respectively, with the temperature and humidity of the air varied. FIG. 5 indicates that V1 serves as a signal that depends only on the humidity without being affected by a variation in ambient temperature T3, which is the temperature of the ambient gas. FIG. 6 shows the results of measurement of the voltage V2 applied to the heating member 4 and measured simultaneously with the measurement of the voltage V1. The heating member 4 has the applied voltages varied by a variation in ambient temperature T3 to serve to maintain the temperature of the air around the heating member 4 constant.

Figure 18:
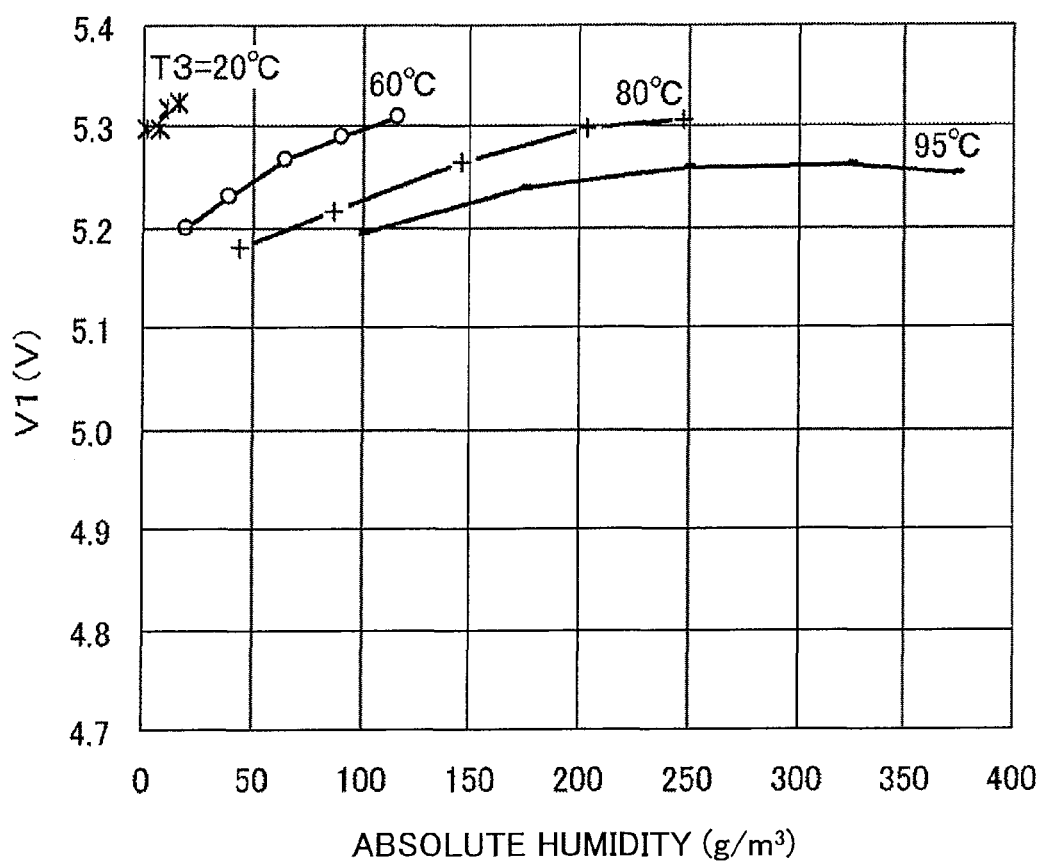
FIG. 18 is a diagram of the results of supplementary experiments for the thermal gas sensor showing the first embodiment.

For comparison, FIG. 18 shows the results of measurement of V1 carried out when only the first heating member 3 driven with the second heating member 4 not driven. The results in FIG. 18 indicate that a variation in ambient temperature T3 significantly varies V1 to prevent characteristics dependent only on the humidity from being obtained. This indicates that provision of the heating member 4 controlled to the predetermined temperature T2 is effective for reducing the dependence of the heating member 3 on the air temperature.

Figure 11:
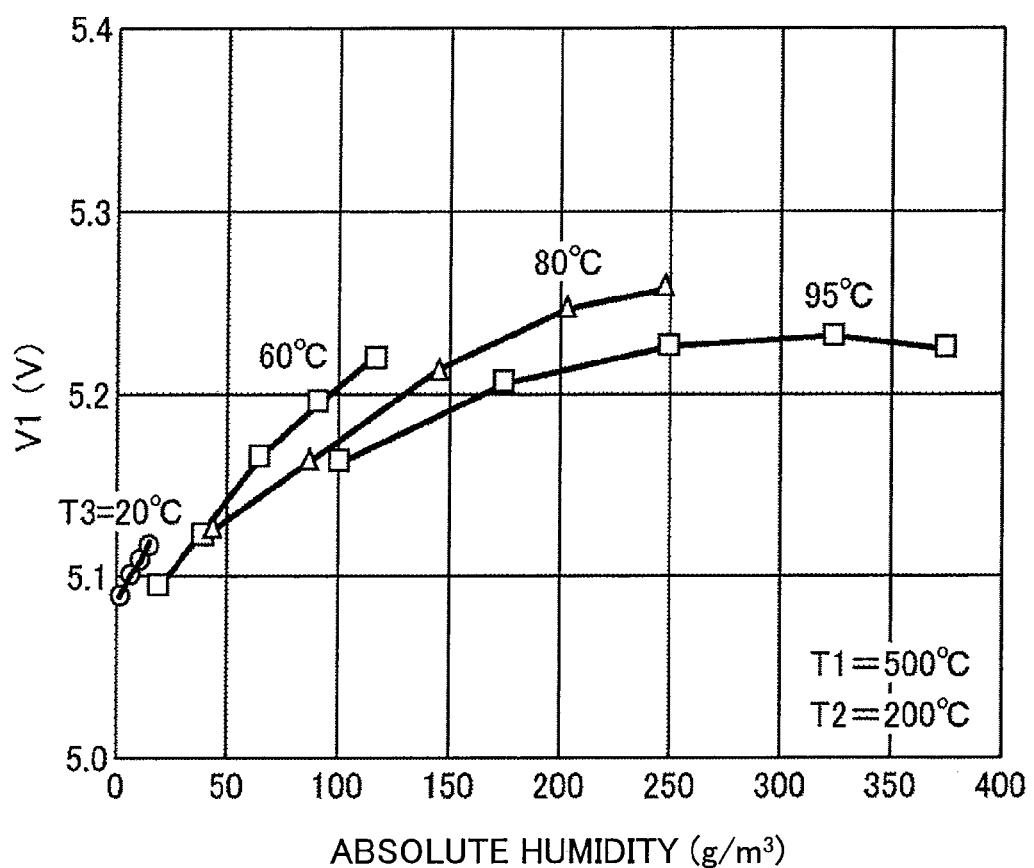
FIG. 11 is a diagram showing the results of experiments for the thermal gas sensor showing the first embodiment.

FIG. 11 shows the results of measurement of the voltage V1 applied to the heating member 3 when the thermal gas sensor according to the present embodiment is installed in the air and when the heating members 3 and 4 are heated so that T1=500° C. and T2=200° C., respectively, with the temperature and humidity of the air varied. When the temperature T2 of the heating member 4 is set to 200° C., dependency on the ambient temperature T3 occurs. This eliminates the effect of the provision of the heating member 4.

Figure 12:
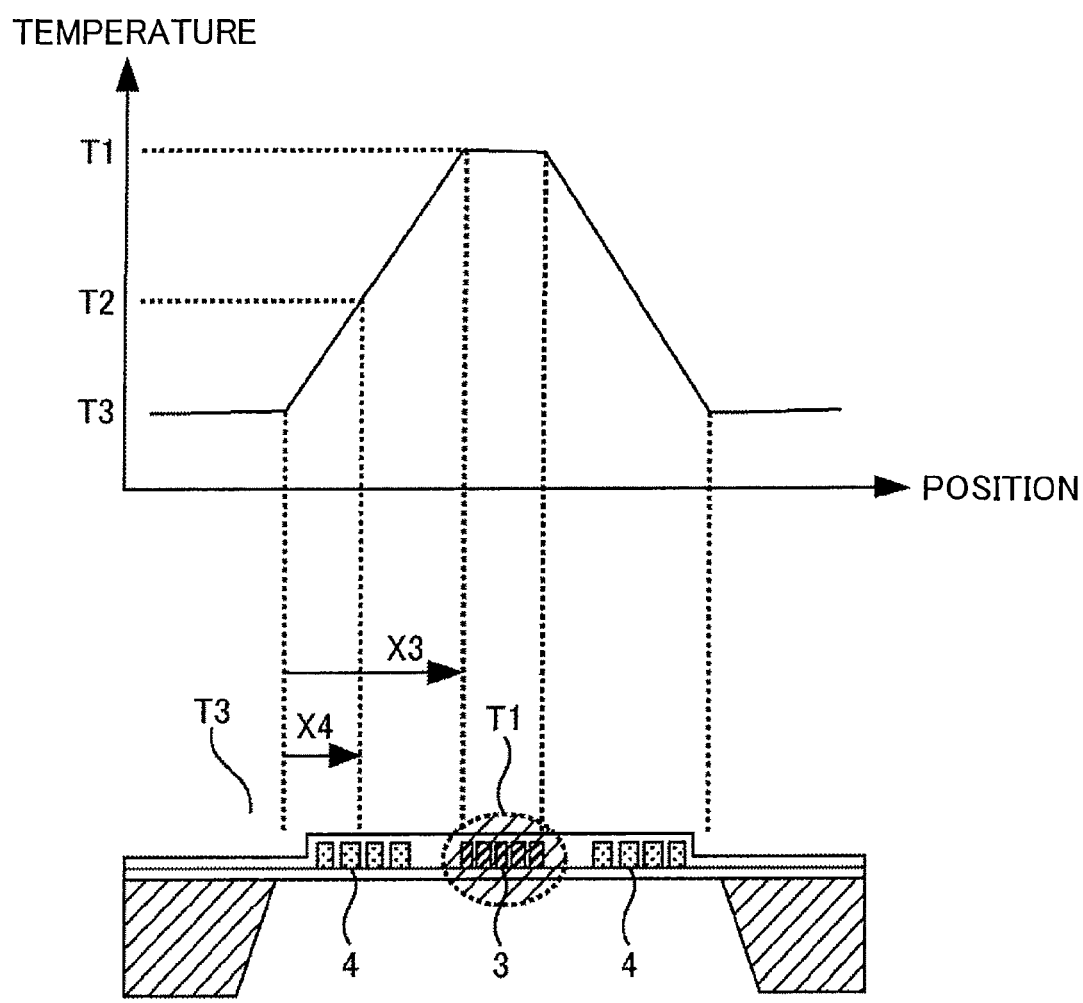
FIG. 12 is a diagram showing the results of experiments for the thermal gas sensor showing the first embodiment.

The reason is as follows. FIG. 12 shows a temperature distribution around the heating member 3 when only the heating member 3 is heated. In this case, the heating member 4 is not heated. The temperature T at any position X between an end of the cavity portion 5 and an end of the heating member 3 has a distribution expressed by:

$$T = T1 \cdot X/X3 + T3 \tag{9}$$

Here, T1 denotes the temperature of the heating member 3, X3 denotes the distance from the end of the cavity portion 5 to the end of the heating member 3, and T3 denotes the ambient temperature. When the distance from the end of the cavity portion 5 to the center of the heating member 4 is denoted by X4, the temperature T2 of the heating member 4 at the position X4 is expressed by:

$$T2 = T1 \cdot X4/X3 + T3 \tag{10}$$

As indicated by Expression (10), even though the heating member 4 is not heated, the temperature of the heating member 4 is raised by heat conduction from the heating member 3. Thus, when the heating temperature of the heating member 4 is set to a value smaller than that calculated by Expression (10), normal heating control is precluded. Hence, the heating temperature T2 of the heating member 4 is desirably set such that:

$$T2 > T1 \cdot X4/X3 + T3 \tag{11}$$

Furthermore, T1 denotes the average temperature of the heating member 3. T2 denotes the average temperature of the heating member 4. T3 denotes the ambient temperature. When T3 is set to be the maximum value within the temperature range of the gas to be measured, measurement can be appropriately achieved all over the gas temperature range.

Moreover, the temperature T2 of the heating member 4 is desirably set to be lower than the temperature T1 of the heating member 3. This is because an increase in the temperature T2 of the heating member 4 reduces the value T1−T2 in Expression (7) and thus the voltage V1 obtained, thus decreasing sensitivity.

As described above, the temperature T2 of the heating member 4 is desirably set such that:

$$T1 \cdot X4/X3 + T3 < T2 < T1 \tag{12}$$

Figure 13:
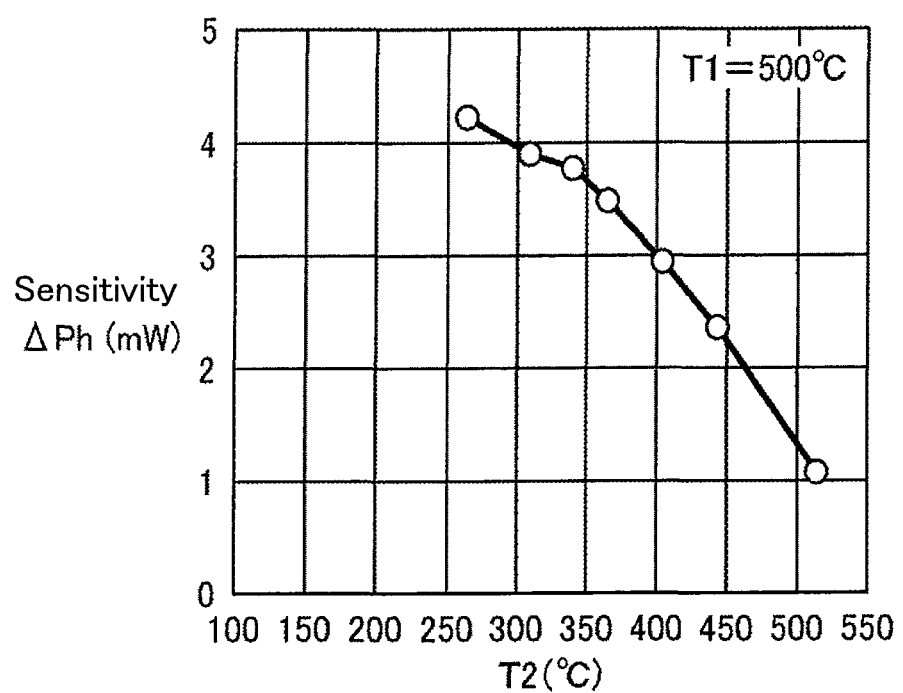
FIG. 13 is a diagram showing the results of experiments for the thermal gas sensor showing the first embodiment.

FIG. 13 shows the results of experiments for the sensitivity with which the humidity is detected when the temperature T2 of the heating member 4 is varied with the temperature T1 of the heating member 3 maintained constant. Here, the sensitivity corresponds to the amount ΔP by which the power consumption of the heating member 3 varies when the humidity is varied. An increase in the temperature T2 of the heating member 4 reduces the sensitivity. This is because the value T1−T2 in Expression (1) decreases as described above. Thus, when T1−T2=0, almost no sensitivity is achieved. Therefore, the temperature T2 of the heating member 4 is desirably set to be lower than the temperature T1 of the heating member 3. Furthermore, when the temperature T2 of the heating member 4 is set to a smaller value within the range indicated by Expression (12), the power consumption can be reduced. As a result, a thermal gas sensor with reduced power consumption is provided.

In the above-described configuration, it is essential that at least the area in which the heating member 4 is laid is larger than that in which the heating member 3 is laid. The increased area in which the heating member 4 is laid enables a further reduction in the adverse effect of a variation in the ambient temperature T3 of the heating member 3.

Furthermore, setting the temperature of the heating member 4 to 100° C., at which water evaporates, enables suppression of a rapid variation in heat conductivity resulting from attachment of droplets.

Additionally, the temperature of the heating member 4 is set to be higher than the range within which the gas temperature is varied by an environmental variation. This is because if the heating member 4 is exposed to gas at a temperature higher than the set temperature of the heating member 4, the heating member 4 conversely needs to be cooled in order to maintain the temperature of the heating member 4 constant. The above-described configuration eliminates the need for a cooling mechanism.

In addition, to allow the humidity in the air to be detected, the temperature of the heating member 3 is desirably set to at least 150° C. This is because when the air temperature is between 100° C. and 150° C., a variation in the heat conductivity in the air associated with the humidity is insignificant, leading to reduced sensitivity.

Furthermore, in the present embodiment, the signal corresponding to the humidity is obtained by means of the voltage applied to the heating member 3. However, the signal corresponding to the humidity is also obtained by measuring the current flowing through the heating member or the voltage applied to the fixed-value resistor 9c.

Second Embodiment

Figure 7:
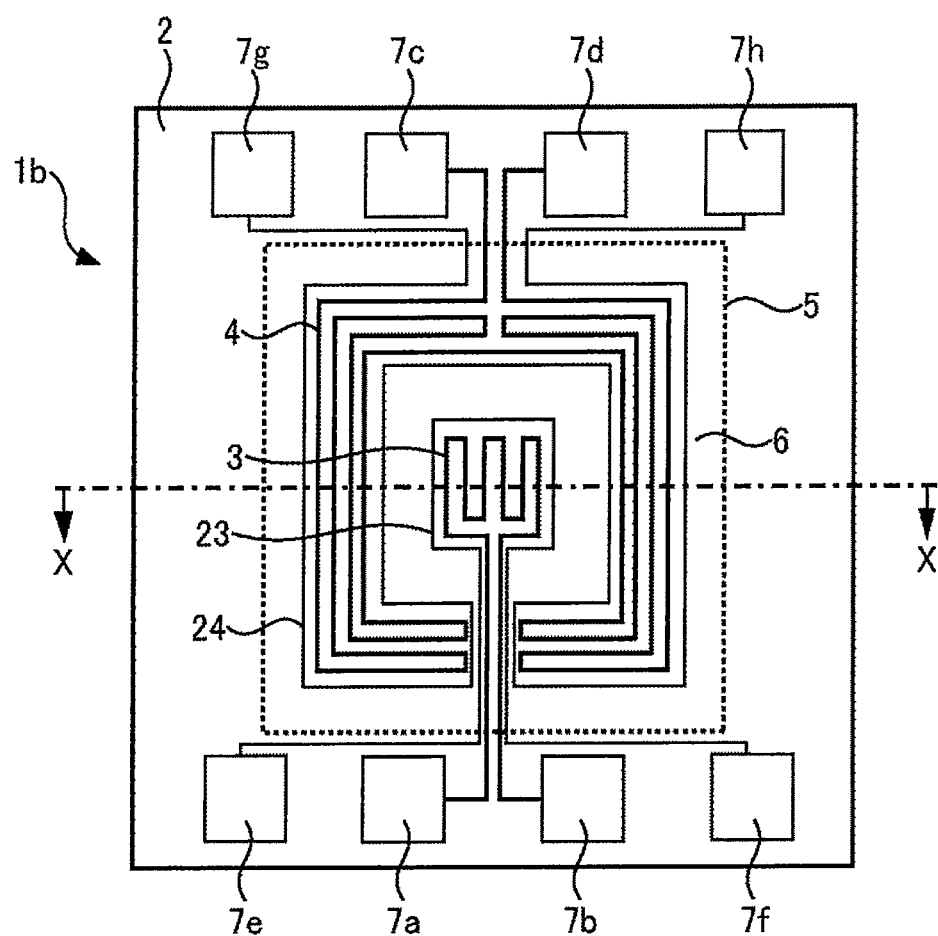
FIG. 7 is a plan view of a thermal gas sensor showing a second embodiment.

FIG. 7 is a plan view of sensor elements of a thermal gas sensor 1b according to a second embodiment of the present invention. The second embodiment is different from the first embodiment shown in FIG. 1 in that a temperature sensor 23 is located near a heating member 3, whereas a temperature sensor 24 is located near a heating member 4. The temperature sensors 23 and 24 are extended in a cavity portion 5 along the heating members 3 and 4, respectively. The temperature sensor 23 mainly detects the temperature of the heating member 3. The temperature sensor 24 mainly detects the temperature of the heating member 4. The temperature sensors 23 and 24 are electrically connected to electrodes 7e, 7f, 7g, and 7h formed on the substrate 2 for connection to an external circuit.

The temperature sensors 23 and 24 are formed similarly to the heating members 3 and 4. A material for the temperature sensors 23 and 24 is selected from platinum (Pt), tantalum (Ta), molybdenum (Mo), silicon (Si), and the like, which are stable at high temperatures (which have high melting points).

Figure 8:
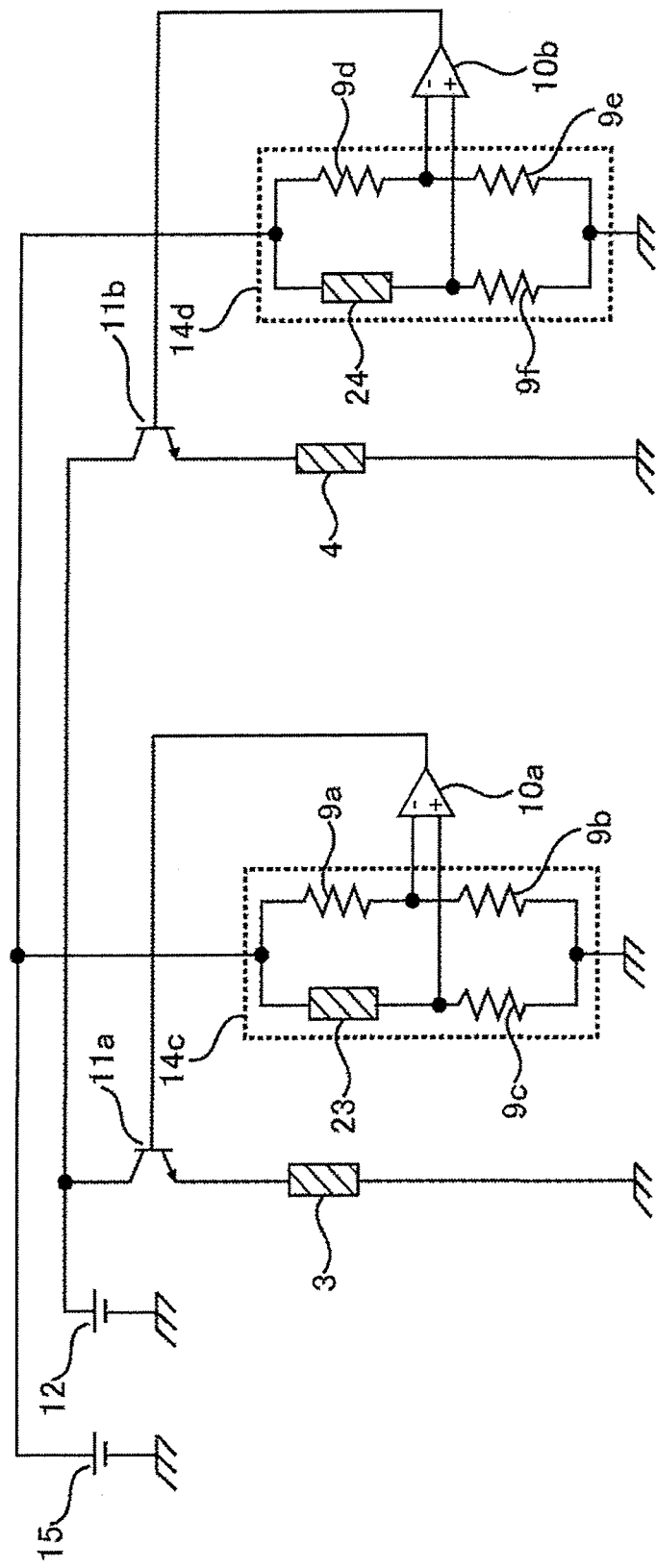
FIG. 8 is a diagram of a driving circuit for the thermal gas sensor showing the second embodiment.

FIG. 8 is a diagram of the configuration of a driving circuit for the thermal gas sensor 1b. The configuration of the driving circuit for the thermal gas sensor 1b according to the second embodiment will be described below with reference to FIG. 8.

The driving circuit for the thermal gas sensor 1b includes a first bridge circuit 14c and a second bridge circuit 14d, differential amplifiers 10a and 10b, and transistors 11a and 11b configured to allow heating current to flow through the heating members 3 and 4. Reference numerals 12 and 15 in FIG. 8 denote power sources.

The first bridge circuit 14c includes the temperature sensor 23 and fixed-value resistors 9a, 9b, and 9c. More specifically, the first bridge circuit 14c includes a series circuit with the temperature sensor 23 and the fixed-value resistor 9c connected together in series and a series circuit with the fixed-value resistors 9a and 9b connected together in series; the series circuits are connected together in parallel. Similarly, the second bridge circuit 14d includes the temperature sensor 24 and fixed-value resistors 9d, 9e, and 9f. More specifically, the second bridge circuit 14d includes a series circuit with the temperature sensor 24 and the fixed-value resistor 9f connected together in series and a series circuit with the fixed-value resistors 9d and 9e connected together in series; the series circuits are connected together in parallel.

In this case, in the first bridge circuit 14c, the potential of the connection end between the temperature sensor 23 and the fixed-value resistor 9c and the potential of the connection end between the fixed-value resistors 9a and 9b are input to the differential amplifier 10a. The differential amplifier 10a outputs a voltage corresponding to the difference between the input voltages to a base electrode of the transistor 11a. The transistor 11a controls a current flowing between a collector and an emitter in accordance with the potential of the base electrode from the power source 12. The emitter electrode of the transistor 11a is connected to the heating member 3 to allow the collector-emitter current to flow through the heating member 3. Thus, the current flowing from the transistor 11a serves to heat the heating member 3. The temperature of the heating member 3 is feedback-controlled to a first temperature T1 that is a constant temperature of about 300° C.

The temperature of the heating member 3 is set such that, based on the known temperature coefficient of resistance of the temperature sensor 23, the ratio of the resistance value of the temperature sensor 23 at the first temperature T1 to the resistance value of the fixed-value resistor 9c is equal to the ratio of the resistance value of the fixed-value resistor 9a to the resistance value of the fixed-value resistor 9b. When the temperature of the temperature sensor 23 is lower than the first temperature T1, the transistor 11a is turned on to allow heating current to flow through the heating member 3. At this time, the temperature of the heating member 3 is almost equivalent to that of the temperature sensor 23.

Similarly, in the second bridge circuit 14d, the potential of the connection end between the temperature sensor 24 and the fixed-value resistor 9f and the potential of the connection end between the fixed-value resistors 9d and 9e are input to the differential amplifier 10b. The differential amplifier 10b outputs a voltage corresponding to the difference between the input voltages to a base electrode of the transistor 11b. The transistor 11b controls a current flowing between a collector and an emitter in accordance with the potential of the base electrode from the power source 12. The emitter electrode of the transistor 11b is connected to the heating member 4 to allow the collector-emitter current to flow through the heating member 4. Thus, the current flowing from the transistor 11b serves to heat the heating member 4. The temperature of the heating member 4 is feedback-controlled to a second temperature T2 that is a constant temperature of about 100° C. At this time, the temperature of the heating member 4 is almost equivalent to that of the temperature sensor 24.

Also in the above-described configuration, the signal corresponding to the humidity is obtained by measuring the voltage applied to the heating member 3.

The present embodiment is advantageous in that the heating members 3 and 4 are electrically disconnected from the bridge circuits 14c and 14d, respectively, eliminating the need to allow a large current for heating to flow through the bridge circuits. Thus, the resistance of the resistor included in each of the bridge circuits 14c and 14d may be set to a large value to reduce the current flowing through the bridge circuit. Furthermore, the voltages applied to the bridge circuits 14c and 14d can be reduced. This reduces power loss in the temperature sensors and resistors included in the bridge circuits 14c and 14d, enabling power saving.

Furthermore, in the present embodiment, a signal corresponding to the humidity is obtained by means of the voltage applied to the heating member 3. However, the signal corresponding to the humidity is also obtained by measuring the current flowing through the heating member.

Third Embodiment

Figure 9:
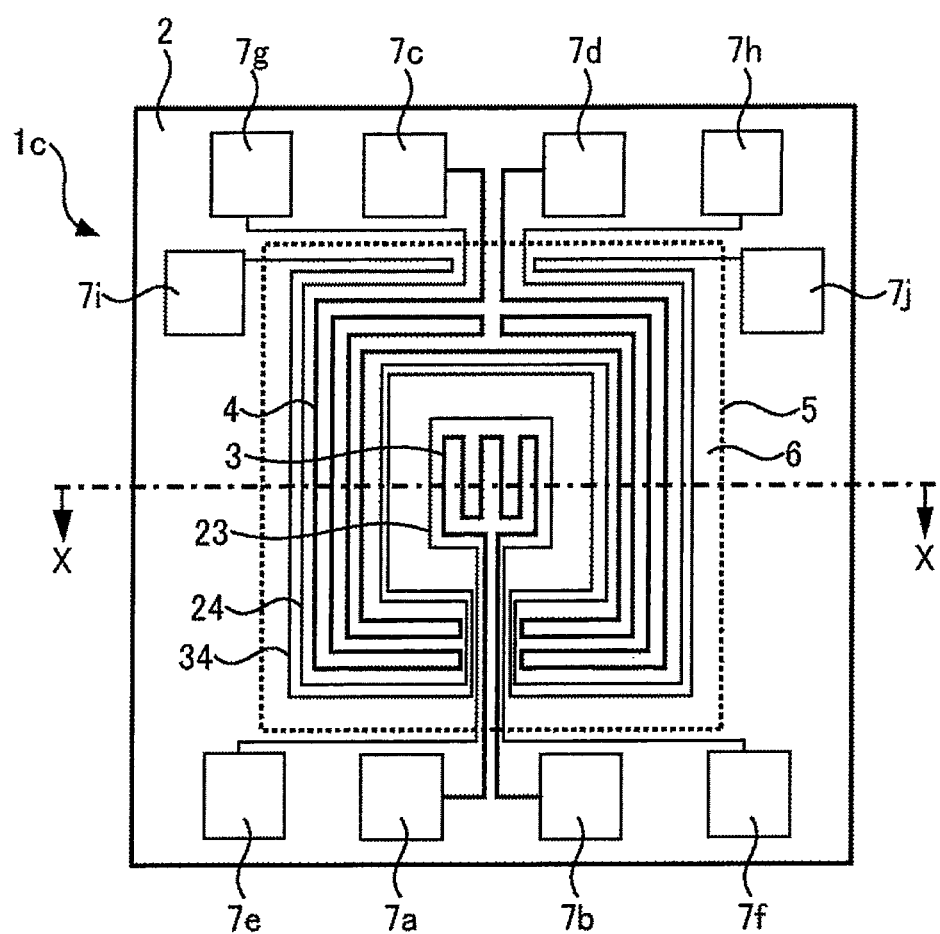
FIG. 9 is a plan view of a thermal gas sensor showing a third embodiment.

FIG. 9 is a plan view of sensor elements of a thermal gas sensor 1c according to a third embodiment of the present invention. The third embodiment is different from the second embodiment shown in FIG. 6 in that in addition to a temperature sensor 24, a temperature sensor 34 is located near a heating member 4. The temperature sensor 34 is extended in a cavity portion 5 along the temperature sensor 24. Like the temperature sensor 24, the temperature sensor 34 mainly detects the temperature of the heating member 4. The temperature sensor 34 is electrically connected to electrodes 7i and 7j formed on the substrate 2 for connection to an external circuit.

The temperature sensor 34 is formed similarly to heating members 3 and 4 and the temperature sensors 23 and 24. A material for the temperature sensor 34 is selected from platinum (Pt), tantalum (Ta), molybdenum (Mo), silicon (Si), and the like, which are stable at high temperatures (which have high melting points).

Figure 10:
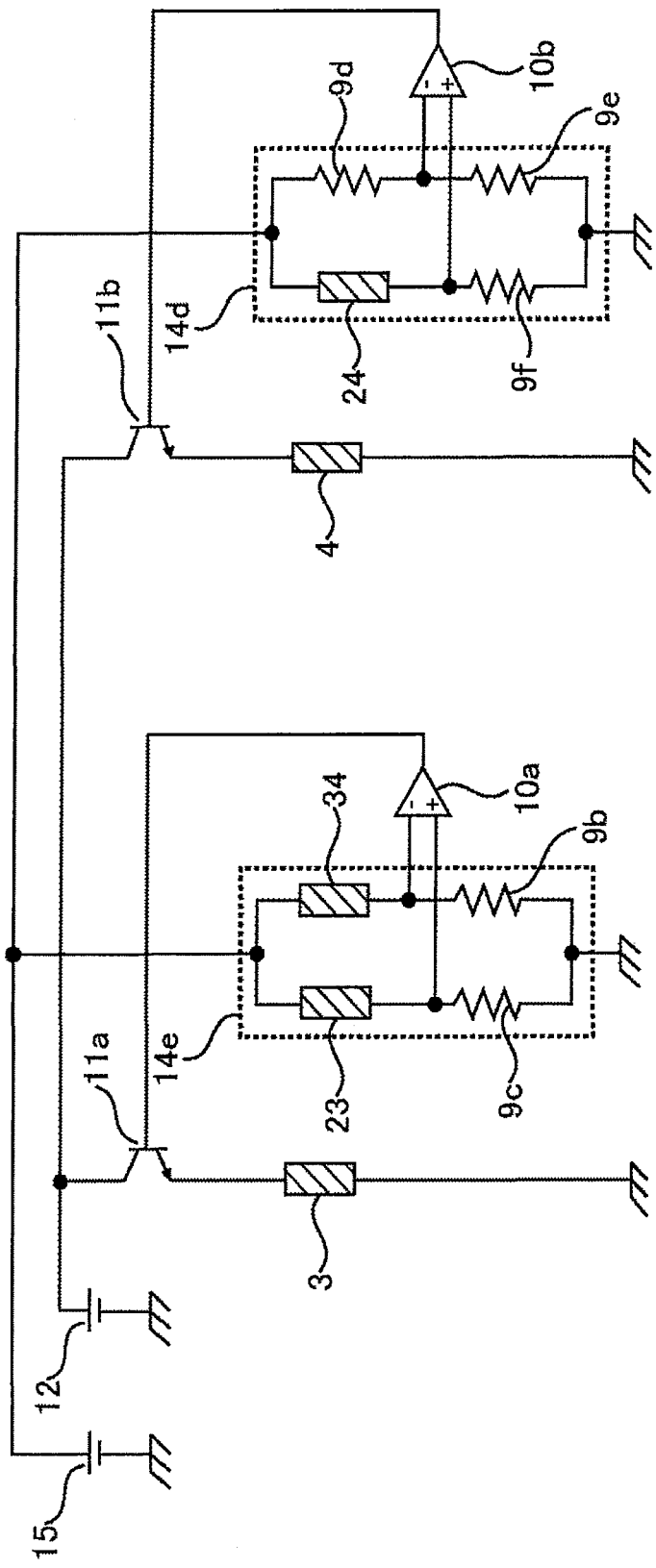
FIG. 10 is a diagram of a driving circuit for the thermal gas sensor showing the third embodiment.

FIG. 10 is a diagram of the configuration of a driving circuit for the thermal gas sensor 1c. The configuration of the driving circuit for the thermal gas sensor 1c according to the third embodiment will be described below with reference to FIG. 10.

The driving circuit for the thermal gas sensor 1c includes a first bridge circuit 14e and a second bridge circuit 14d, differential amplifiers 10a and 10b, and transistors 11a and 11b configured to allow heating current to flow through the heating members 3 and 4. Reference numerals 12 and 15 in FIG. 10 denote power sources.

The first bridge circuit 14e includes the temperature sensor 23, the temperature sensor 34, and fixed-value resistors 9b and 9c. More specifically, the first bridge circuit 14e includes a series circuit with the temperature sensor 23 and the fixed-value resistor 9c connected together in series and a series circuit with the temperature sensor 34 and the fixed-value resistor 9b connected together in series; the series circuits are connected together in parallel. The second bridge circuit 14d includes the temperature sensor 24 and fixed-value resistors 9d, 9e, and 9f. More specifically, the second bridge circuit 14d includes a series circuit with the temperature sensor 24 and the fixed-value resistor 9f connected together in series and a series circuit with the fixed-value resistors 9d and 9e connected together in series; the series circuits are connected together in parallel.

In this case, in the first bridge circuit 14e, the potential of the connection end between the temperature sensor 23 and the fixed-value resistor 9c and the potential of the connection end between the temperature sensor 34 and the fixed-value resistor 9b are input to the differential amplifier 10a. The temperature of the heating member 3 is feedback-controlled to a first temperature T1. At this time, the temperature of the heating member 3 is almost equivalent to that of the temperature sensor 23.

The temperature of the heating member 3 is set such that, based on the known temperature coefficient of resistance of the temperature sensor 23 and the temperature sensor 34, the ratio of the resistance value of the temperature sensor 23 at the first temperature T1 to the resistance value of the fixed-value resistor 9c is equal to the ratio of the resistance value of the temperature sensor 34 at a second temperature T2 to the resistance value of the fixed-value resistor 9b. When the temperature of the temperature sensor 23 is lower than the first temperature T1, the transistor 11a is turned on to allow heating current to flow through the heating member 3.

This also applies to the second bridge circuit 14d as described in Embodiment 2.

In the present embodiment, the temperature of the heating member 3 is controlled so as to be higher than the temperature T2 of the heating member 4 by a given value. Thus, the heating member 3 is controlled to the first temperature T1.

Also in the above-described configuration, a signal corresponding to the humidity is obtained by measuring the voltage applied to the heating member 3.

In the present embodiment, the heating members 3 and 4 are electrically disconnected from the bridge circuits 14e and 14d, respectively, eliminating the need to allow a large current for heating to flow through the bridge circuits. Thus, the resistance of each of the temperature sensors and resistors included in the bridge circuits 14e and 14d may be set to a large value. Furthermore, the voltages applied to the bridge circuits 14e and 14d can be reduced.

Moreover, even if a current flowing through the temperature sensor 34 included in the bridge circuit 14e results in power consumption, since the current contributes to raising the temperature of the heating member 4, the power can be effectively utilized. This reduces power loss in the resistors included in the bridge circuits 14c and 14d, enabling power saving.

Furthermore, when the temperature sensors 23 and 34 are formed of the same material, resistance characteristics and processing conditions are the same for both temperature sensors. This improves resistance balance, enabling a reduction in the degradation of the resistance balance caused by a processing variation.

Fourth Embodiment

Figure 14:
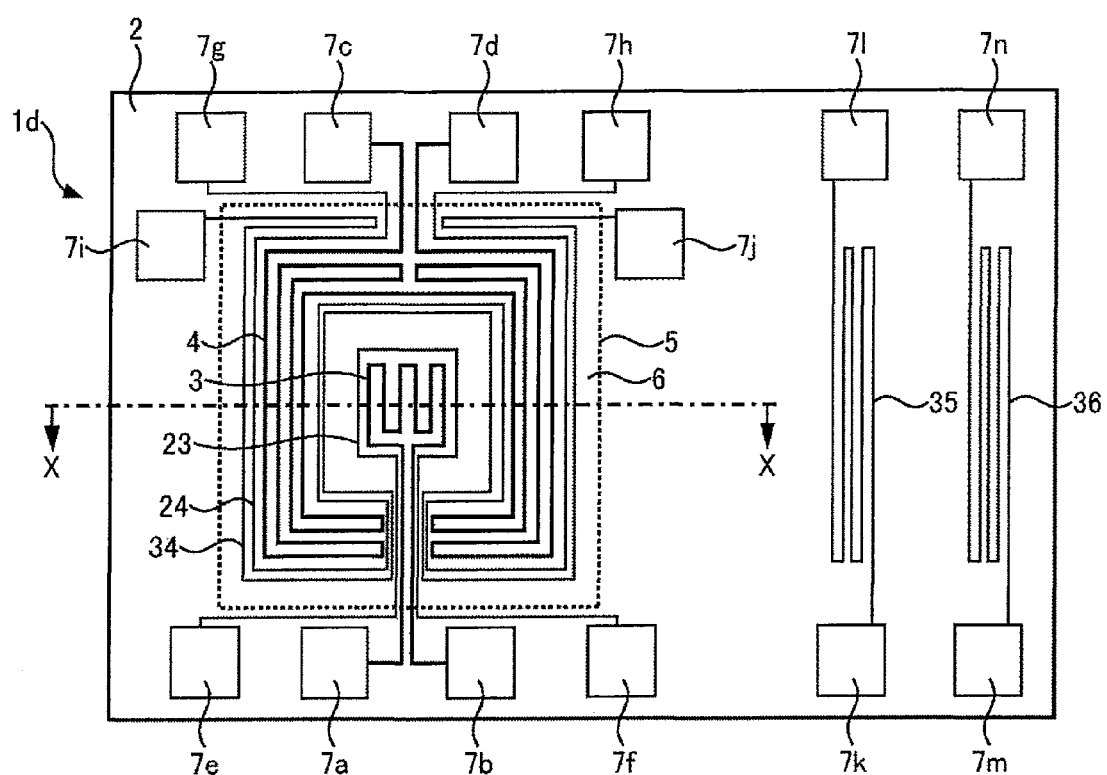
FIG. 14 is a plan view of a thermal gas sensor showing a fourth embodiment.

FIG. 14 is a plan view of sensor elements of a thermal gas sensor 1d according to a fourth embodiment of the present invention. The fourth embodiment is different from the third embodiment shown in FIG. 9 in that temperature sensors 35 and 36 are arranged on the thermal gas sensor 11d. The temperature sensors 35 and 36 are arranged outside the cavity portion 5 to mainly detect the ambient temperature. The temperature sensor 35 is electrically connected to electrodes 7k and 7l formed on a substrate 2 for connection to an external circuit. Furthermore, the temperature sensor 36 is electrically connected to electrodes 7m and 7n formed on the substrate 2 for connection to an external circuit.

The temperature sensors 35 and 36 are formed similarly to heating members 3 and 4 and temperature sensors 23 and 24. A material for the temperature sensors 35 and 36 is selected from platinum (Pt), tantalum (Ta), molybdenum (Mo), silicon (Si), and the like, which are stable at high temperatures (which have high melting points).

Figure 15:
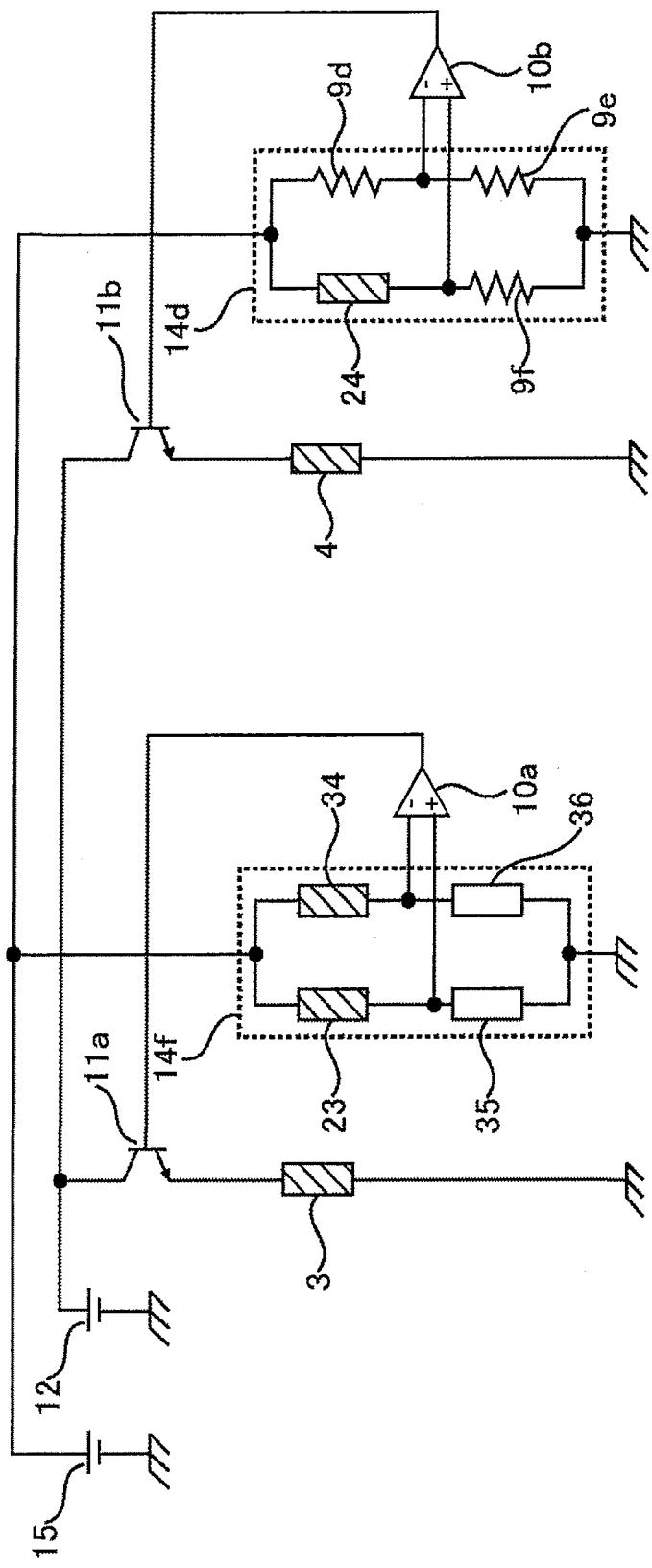
FIG. 15 is a diagram of a driving circuit for the thermal gas sensor showing the fourth embodiment.

FIG. 15 is a diagram of the configuration of a driving circuit for the thermal gas sensor 1d. The configuration of the driving circuit for the thermal gas sensor 1d according to the fourth embodiment will be described below with reference to FIG. 15.

The driving circuit for the thermal gas sensor 1d includes a first bridge circuit 14f and a second bridge circuit 14d, differential amplifiers 10a and 10b, and transistors 11a and 11b configured to allow heating current to flow through the heating members 3 and 4. Reference numerals 12 and 15 in FIG. 14 denote power sources.

The first bridge circuit 14f includes the temperature sensor 23, a temperature sensor 34, and the temperature sensors 35 and 36. More specifically, the first bridge circuit 14f includes a series circuit with the temperature sensors 23 and 35 connected together in series and a series circuit with the temperature sensors 34 and 36 connected together in series; the series circuits are connected together in parallel. The second bridge circuit 14d includes the temperature sensor 24 and fixed-value resistors 9d, 9e, and 9f. More specifically, the second bridge circuit 14d includes a series circuit with the temperature sensor 24 and the fixed-value resistor 9f connected together in series and a series circuit with the fixed-value resistors 9d and 9e connected together in series; the series circuits are connected together in parallel.

In this case, in the first bridge circuit 14f, the potential of the connection end between the temperature sensors 23 and 35 and the potential of the connection end between the temperature sensors 34 and 36 are input to the differential amplifier 10a. The differential amplifier 10a outputs a voltage corresponding to the difference between the input voltages to a base electrode of the transistor 11a. The transistor 11a controls a current flowing between a collector and an emitter in accordance with the potential of the base electrode. The emitter electrode of the transistor 11b is connected to the heating member 3 to allow the collector-emitter current to flow through the heating member 3. Thus, the heating member 3 is heated and feedback-controlled to a first temperature T1. At this time, the temperature of the heating member 3 is almost equivalent to that of the temperature sensor 23. Furthermore, the temperature of the temperature sensor 35 is almost equivalent to that of the temperature sensor 36.

The temperature of the heating member 3 is set such that, based on the known temperature coefficient of resistance of the temperature sensor 23 and the temperature sensor 34, the ratio of the resistance value of the temperature sensor 23 at the first temperature T1 to the resistance value of the temperature sensor 35 is equal to the ratio of the resistance value of the temperature sensor 34 at a second temperature T2 to the resistance value of the temperature sensor 36. When the temperature of the temperature sensor 23 is lower than the first temperature T1, the transistor 11a is turned on to allow heating current to flow from the power source 12 to the heating member 3 via the transistor 11a.

This also applies to the second bridge circuit 14d as described in Embodiment 2.

In the present embodiment, the temperature of the heating member 3 is controlled so as to be higher than the temperature T2 of the heating member 4 by a given value. Thus, the heating member 3 is controlled to the first temperature T1.

Also in the above-described configuration, a signal corresponding to the humidity is obtained by measuring the voltage applied to the heating member 3.

In the present embodiment, the temperature sensors 23, 34, 35, and 36 included in the bridge circuit 14f are formed of the same material. Thus, the resistance characteristics and processing conditions are the same for all the temperature sensors. This improves the resistance balance. Furthermore, the degradation of the resistance balance associated with processing can be reduced.

Additionally, heat generated by currents flowing through the temperature sensors 35 and 36 raises the temperature of the thermal gas sensor 1d, contributing to raising the temperatures of the heating members 3 and 4. If a fixed-value resistor is used, since the fixed-value resistor is provided away from the thermal gas sensor 1d, heat generated by a current flowing through the fixed-value resistor is radiated to the surroundings. Thus, the heat fails to contribute to raising the temperature of the heating members 3 and 4. Therefore, the present embodiment allows power to be effectively used, enabling a reduction in power required. Furthermore, all the resistors included in the bridge circuit 14f can be formed inside the elements of the thermal gas sensor 1d. This enables a reduction in the number of components required and thus in the size of the thermal gas sensor 1d.

Moreover, as shown in FIG. 15, when the fixed-value resistors 9f and 9e are formed in the thermal gas sensor 1d similarly to the temperature sensors 35 and 36, the size of the thermal gas sensor 1d can further be reduced.

Fifth Embodiment

Figure 16:
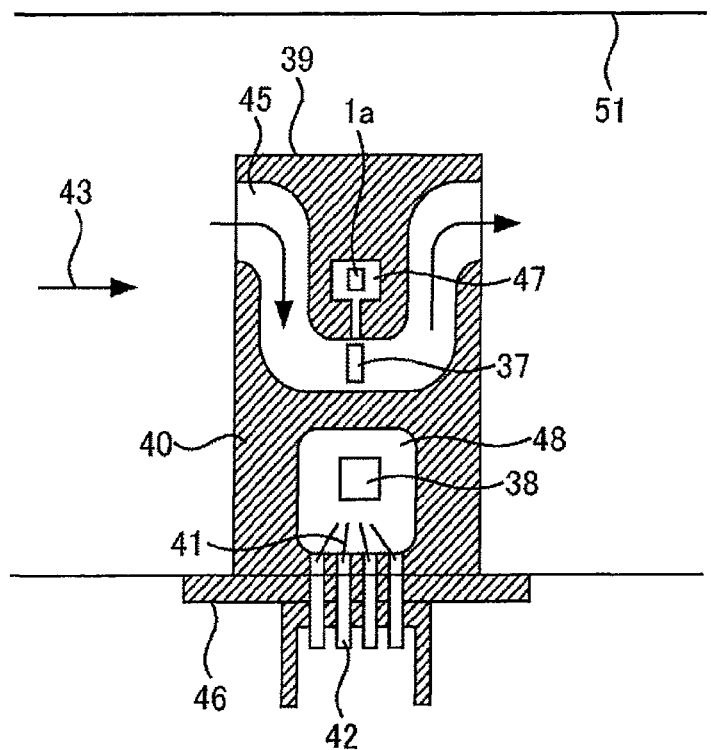
FIG. 16 is a plan view of a thermal flowmeter showing a fifth embodiment.
Figure 17:
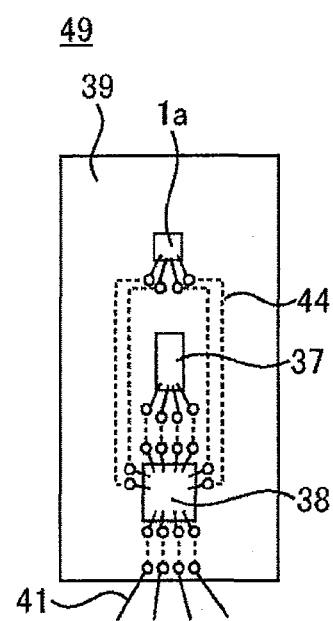
FIG. 17 is an electric connection diagram of a composite sensor showing the fifth embodiment.

FIGS. 16 and 17 are plan views showing a thermal flowmeter 46 with a composite sensor 49 to which the thermal gas sensor 1a shown in Embodiment 1 is applied and which is provided integrally with a thermal airflow rate sensor 37. The thermal flowmeter 46 according to the present embodiment is mounted, for example, in an intake pipe 51 in an internal combustion engine. The thermal gas sensor 1a, the thermal airflow rate sensor 37, and a driving LSI 38 are installed on a base member 39. Furthermore, a housing member 40 provided so as to cover the base member 39 forms a sub-passage 45 configured to take in an airflow 43 and cavity portions 47 and 48. The thermal airflow rate sensor 37 is installed in the sub-passage 45. The cavity portion 47 is in communication with the sub-passage 45. The thermal gas sensor 1a is installed in the cavity portion 47. The driving LSI 38 is installed in the cavity portion 48.

Now, electric connections of the composite sensor 49 will be described with reference to FIG. 17. The thermal gas sensor 1a is connected to the driving LSI 38 via an inner layer conductor 44 provided inside the base member 39 using bonding wires such as gold wires. Dotted lines in FIG. 17 show the inner layer conductor 44. The thermal airflow rate sensor 37 is also connected to the driving LSI 38 via the inner layer conductor 44 provided inside the base member 39 using bonding wires such as gold wires. The driving LSI 38 includes a circuit configured to drive the thermal gas sensor 1a and a circuit configured to drive the thermal airflow rate sensor 37. The driving LSI 38 loads an electric signal related to the humidity from the thermal gas sensor 1a and an electric signal related to an air mass flow rate from the thermal airflow rate sensor 37. The driving LSI 38 is connected to a terminal section 42 through bonding wires 41 of aluminum or the like via bonding wires such as gold wires and the inner layer conductor. The signals related to the humidity and the airflow rate can be transmitted from the terminal section 42 to an external circuit.

An arithmetic unit is mounted in the driving LSI 38 to execute calculations using the signal from the thermal airflow rate sensor 37 and the signal from the thermal gas sensor. The composite sensor can thus correct errors resulting from the dependence of the thermal airflow rate sensor 37 on the humidity. Hence, the airflow rate can be accurately calculated and output.

What is claimed is:

1. A thermal gas sensor comprising:
   a substrate with a cavity portion;
   a thin-film support stacked in the cavity portion and comprising a plurality of insulating layers; and
   a first heating member and a second heating member both sandwiched between the insulating layers in the thin-film support,
   wherein the second heating member is located around a periphery of the first heating member,
   the first heating member is controlled to a temperature higher than a temperature to which the second heating member is controlled,
   a driving circuit that holds relatively constant the temperature to which the second heating member is controlled, and
   a concentration of an ambient gas is measured based on current applied to the first heating member, and
   wherein the second heating member is formed to surround the first heating member on all sides thereof, and an area in which the second heating member is laid is formed to be larger than an area in which the first heating member is laid.

2. The thermal gas sensor according to claim 1, wherein the first and second heating members are subjected to heating control in such a manner that there is a given difference in temperature between the first heating member and the second heating member.

3. The thermal gas sensor according to claim 1, wherein a first temperature sensor is located in proximity to the first heating member.

4. The thermal gas sensor according to claim 3, wherein the heating temperature of the first heating member is controlled by heating temperature control means with a bridge circuit comprising the first temperature sensor and a plurality of fixed-value resistors.

5. The thermal gas sensor according to claim 1, wherein the second heating member is heated to 100° C. or higher.

6. The thermal gas sensor according to claim 1, wherein a heating temperature of the first heating member is controlled by heating temperature control means with a bridge circuit comprising the first heating member and a plurality of fixed-value resistors.

7. The thermal gas sensor according to claim 1, wherein when the heating temperature of the first heating member is denoted by T1, the heating temperature of the second heating member is denoted by T2, a gas temperature around the thermal gas sensor is denoted by T3, a distance from an end of the cavity portion to the first heating member is denoted by X3, and a distance from an end of the cavity portion to the second heating member is denoted by X4, the heating temperature T2 of the second heating member is set such that T1·X4/X3+T3<T2<T1.

8. A thermal gas sensor comprising:
a substrate with a cavity portion;
a thin-film support stacked in the cavity portion and comprising a plurality of insulating layers; and
a first heating member and a second heating member both sandwiched between the insulating layers in the thin-film support,
wherein the second heating member is located around a periphery of the first heating member,
the first heating member is controlled to a temperature higher than a temperature to which the second heating member is controlled, and
a concentration of an ambient gas is measured based on current applied to the first heating member,
wherein the second heating member is formed to surround the first heating member on all sides thereof, and an area in which the second heating member is laid is formed to be larger than an area in which the first heating member is laid,
wherein a second temperature sensor is located in proximity to the second heating member.

9. The thermal gas sensor according to claim 8, wherein the heating temperature of the second heating member is controlled by heating temperature control means with a bridge circuit comprising the second temperature sensor and a plurality of fixed-value resistors.

10. A thermal gas sensor comprising:
a substrate with a cavity portion;
a thin-film support stacked in the cavity portion and comprising a plurality of insulating layers; and
a first heating member and a second heating member both sandwiched between the insulating layers in the thin-film support,
wherein the second heating member is located around a periphery of the first heating member,
the first heating member is controlled to a temperature higher than a temperature to which the second heating member is controlled, and
a concentration of an ambient gas is measured based on current applied to the first heating member,
wherein the second heating member is formed to surround the first heating member on all sides thereof, and an area in which the second heating member is laid is formed to be larger than an area in which the first heating member is laid,
wherein a first temperature sensor is located in proximity to the first heating member,
wherein a second temperature sensor is located in proximity to the second heating member, and
the heating temperature of the first heating member is controlled by a bridge circuit with the first temperature sensor and the second temperature sensor and heating temperature control means with the bridge circuit.

11. A thermal gas sensor comprising:
a substrate with a cavity portion;
a thin-film support stacked in the cavity portion and comprising a plurality of insulating layers; and
a first heating member and a second heating member both sandwiched between the insulating layers in the thin-film support,
wherein the second heating member is located around a periphery of the first heating member,
the first heating member is controlled to a temperature higher than a temperature to which the second heating member is controlled, and
a concentration of an ambient gas is measured based on current applied to the first heating member,
wherein the second heating member is formed to surround the first heating member on all sides thereof, and an area in which the second heating member is laid is formed to be larger than an area in which the first heating member is laid,
wherein a heating temperature of the second heating member is controlled by heating temperature control means with a bridge circuit comprising the second heating member and a plurality of fixed-value resistors.

12. A concentration detection apparatus including a thermal gas sensor, the apparatus comprising:
a base member, a thermal airflow rate sensor located on the base member, and a driving integrated circuit electrically connected to the thermal airflow rate sensor,
wherein the thermal gas sensor is located on the base member and electrically connected to the driving integrated circuit via an inner layer conductor provided on the base member, wherein the thermal gas sensor comprises:
a substrate with a cavity portion;
a thin-film support stacked in the cavity portion and comprising a plurality of insulating layers; and
a first heating member and a second heating member both sandwiched between the insulating layers in the thin-film support,
wherein the second heating member is located around a periphery of the first heating member,
the first heating member is controlled to a temperature higher than a temperature to which the second heating member is controlled, and
a concentration of an ambient gas is measured based on current applied to the first heating member,
wherein the second heating member is formed to surround the first heating member on all sides thereof, and an area in which the second heating member is laid is formed to be larger than an area in which the first heating member is laid.

13. A thermal flowmeter comprising a housing, a sub-passage provided in the housing to take in an airflow, a first cavity portion configured to communicate with the sub-passage, a thermal airflow rate sensor located in the sub-passage, and a thermal gas sensor located in the first cavity portion, wherein the thermal gas sensor comprises a substrate with a second cavity portion, a thin-film support stacked in the second cavity portion and comprising a plurality of insulating layers, and a first heating member and a second heating member both sandwiched between the insulating layers in the thin-film support, wherein the second heating member is located around a periphery of the first heating member, the first heating member is controlled to a temperature higher than a temperature to which the second temperature is controlled, and a concentration of ambient gas is measured based on power applied to the first heating member.

* * * * *